United States Patent
de Lint (10) Patent No.: US 7,033,330 B2
(45) Date of Patent: Apr. 25, 2006

(54) WRIST BRACE

(75) Inventor: Jan Andries de Lint, Oosterhout (NL)

(73) Assignee: Ortlint B.V., Oosterhout (NL)

( * ) Notice: Subject to any disclaimer, the term of this patent is extended or adjusted under 35 U.S.C. 154(b) by 18 days.

(21) Appl. No.: 10/239,132

(22) PCT Filed: Mar. 20, 2001

(86) PCT No.: PCT/NL01/00226

§ 371 (c)(1),
(2), (4) Date: Dec. 10, 2002

(87) PCT Pub. No.: WO01/70148

PCT Pub. Date: Sep. 27, 2001

(65) Prior Publication Data

US 2004/0024339 A1    Feb. 5, 2004

(30) Foreign Application Priority Data

Mar. 20, 2000  (NL) .................................... 1014695

(51) Int. Cl.
*A61F 5/00* (2006.01)

(52) U.S. Cl. .............................. 602/20; 602/5; 602/16; 602/21

(58) Field of Classification Search .................... 602/5, 602/16, 20, 21, 60, 62, 64; 128/869, 878, 128/879, 881

See application file for complete search history.

(56) References Cited

U.S. PATENT DOCUMENTS

| | | | |
|---|---|---|---|
| 4,677,971 A * | 7/1987 | Lindemann | 602/21 |
| 4,790,300 A * | 12/1988 | Marx | 602/21 |
| 4,949,711 A * | 8/1990 | Gyovai et al. | 602/21 |
| 5,002,044 A | 3/1991 | Carter | |
| 5,103,807 A * | 4/1992 | Makaran | 601/40 |
| 5,254,078 A * | 10/1993 | Carter et al. | 602/21 |
| 5,358,471 A * | 10/1994 | Klotz | 602/21 |
| 5,364,323 A | 11/1994 | Liu | |
| 5,417,645 A * | 5/1995 | Lemmen | 602/21 |
| 5,653,680 A | 8/1997 | Cruz | |
| 5,672,150 A * | 9/1997 | Cox | 602/21 |
| 5,868,692 A * | 2/1999 | Michniewicz | 602/21 |
| 5,876,363 A * | 3/1999 | Marx | 602/21 |

(Continued)

FOREIGN PATENT DOCUMENTS

GB    104 601 A    4/1917

(Continued)

*Primary Examiner*—Henry Bennett
*Assistant Examiner*—Amanda Wieker
(74) *Attorney, Agent, or Firm*—Martin Fleit; Paul D. Bianco; Fleit Kain Gibbons Gutman Bongini & Bianco, P.L.

(57) ABSTRACT

A wrist brace for relaxing extensor musculature in a forearm having a first body, a second body, and at least one hinge joint hinging the first and second body together. The first body is arranged to be secured to a forearm while the second body extends from the hinge to a palm of the hand belonging to the forearm. A force generator, such as a leaf spring, is adapted to generate a moment of force between the first and second body, such that the second body, hinging relative to the first body, presses against the palm of the hand in a direction directed towards the upper side of the hand belonging to the palm, and wherein the moment of force is at least exerted on the hand when the hand is extended in line with the forearm.

24 Claims, 8 Drawing Sheets

U.S. PATENT DOCUMENTS

| | | | | |
|---|---|---|---|---|
| 6,443,918 B1 * | 9/2002 | Wang | ............................. | 602/5 |
| 6,716,185 B1 * | 4/2004 | Rieger | ......................... | 602/21 |
| 6,718,656 B1 * | 4/2004 | Houser et al. | .................. | 36/88 |
| 6,723,061 B1 * | 4/2004 | Williams | ..................... | 602/21 |

FOREIGN PATENT DOCUMENTS

| | | |
|---|---|---|
| GB | 2 184 659 | 7/1987 |
| WO | WO 96/34211 | * 10/1996 |
| WO | WO 99/52477 | 10/1999 |

* cited by examiner

WRIST BRACE

BACKGROUND OF THE INVENTION

The invention relates to an aid for relaxing the extensor musculature in the forearm.

The invention also relates to a method for relaxing the extensor musculature in the forearm.

SUMMARY OF THE INVENTION

The aid and method according to the invention are both based on the principle of the flexor-extensor antagonism and can be used for physiologically relaxing an extensor musculature. This extensor musculature is an extensor muscle, i.e. an extensor in the forearm which is connected to the lateral epicondyle. The extensor musculature is in antagonistic action with the flexor musculature.

The object of the invention is to relax the extensor musculature in the forearm. To this end, an aid according to the invention is characterized in that it is provided with a first body, a second body and at least one hinge joint hinging the first and the second body together, the first body being arranged to be secured to a forearm while the second body extends from the hinge to a palm of the hand belonging to the forearm, the aid being further provided with resilient means which, in use, generate a moment of force between the first and second body such that the second body, hinging relative to the first body, presses against the palm of the hand in a direction directed towards the upper side of the hand belonging to the palm. In the forearm to which the aid is secured, a wearer of the above-mentioned aid will experience a moment of force equivalent to a moment of force which is created by flexing the extensor musculature. As a result, the flexor musculature will be flexed. The extensor musculature is thereby physiologically relaxed. Relaxation of the extensor musculature is one of the possible applications of the invention which can be of interest in the case of injured extensor musculature. An example of an injured extensor musculature is a so-called tennis elbow. Such an injury occurs frequently. This injury results in pain stimuli coming from the origin of the extensor musculature at the elbow. This origin is the epicondyle. Physiological relaxation of the extensor musculature reduces the pain stimuli and promotes recovery of the injury. Heretofore, in case of an injury to the extensor musculature, use is made of straps being tied around the forearm. Although these straps provide some support to the extensor musculature, the extensor musculature is thereby hardly relaxed, if at all.

Preferably, the first body is provided with a first channel-shaped member of a rigid material. In particular, the first channel-shaped member is arranged to embrace, in use, at least a part of an underside of the forearm. It has been found that with this variant, attachment to the forearm is best to generate the desired moment of force.

Further, it is preferred that the second body is provided with a second channel-shaped member of a rigid material.

In particular, the second channel-shaped member is arranged to abut, during use, against at least a part of an inside of the hand situated between the index finger and the little finger.

According to a highly advanced embodiment of the aid according to the invention, the first channel-shaped member is provided with a first and second side wall situated opposite each other, the second channel-shaped member is provided with a first and second side wall situated opposite each other, and the at least one hinge comprises a first and second hinge, the first hinge hinging the first side walls together around a rotation axis and the second hinge hinging the second side walls together around the rotation axis. It has been found that such an aid can be very easily worn without the user suffering much hindrance. Also, it is hardly, if at all, visible that the user is wearing the aid. Moreover, clothing can be worn in the normal manner.

In particular, the first hinge is provided with a first metal resilient bar-shaped member having a first and second end which are connected to the first side walls of the first and second channel-shaped member, respectively, and the second hinge is provided with a second metal resilient bar-shaped member having a first and second end connected to the second side walls of the first and second channel-shaped member, respectively, the first and second bar-shaped members forming the resilient means.

A particular advantage of this embodiment is that the hinges can work, without friction and noise.

Due to the resilient means and the hinge being integrated in the first and second metal, flexible bar-shaped member, the aid can be designed to be very compact, which, again, offers great advantages for a user when wearing the aid.

According to a highly advanced embodiment, the resilient means are provided with memory metal. Such a material has a number of very special properties. For instance, large elastic deformation is possible. Further, the material comprises a very low rigidity modulus when the material stress reaches the so-called plateau stress. Such an arrangement has the advantage that with a selected initial moment of force in a particular position of the hand relative to the arm, the moment of force will change only slightly with an increasing or decreasing angle of bend. This is caused by the relatively low spring constant. As a result of all this, a substantially constant flexiforce, that is, moment of force is exerted on the hand, independently of the position the hand takes around the wrist joint relative to the forearm.

In particular, the first and second bar-shaped member are manufactured from, the memory metal.

Preferably, the memory metal comprises a memory alloy in austenitic condition. As a result of all this, the first and the second bar-shaped member can have a length varying between 40 mm and 120 mm. The first and the second bar-shaped member can have a diameter of 0.5 mm to 2 mm. Further, the above-mentioned advantage of the substantially constant moment of force is present.

A favorable embodiment of the aid according to the invention is characterized in that the first body is substantially tubular and is provided with a channel-shaped member of a rigid material, and a first elastically adjustable strap connected to the channel-shaped member, the channel-shaped member being arranged to embrace, in use, at least a part of an upper side of the forearm while the first strap bridges an open longitudinal-side of the channel-shaped-member, thereby passing over at least a part of the underside of the forearm. With the first, elastically adjustable strap, provided to that end with, for instance, a hook and loop type tape closure or clasps, such as VELCRO®, the first body can be secured to the forearm. The second body of the aid should be connected to the hand of the forearm. To this end, a further elaborated embodiment according to the invention is characterized in that the second body is arranged to embrace the part of the hand situated between the fingers and the thumb. Preferably, the hand is then only party covered, so that it can continue to perform its gripping functions substantially completely. In a special embodiment, the aid is further characterized in that the second body has a substantially tubular design and is manufactured from a rigid material.

An advantageous embodiment of the aid according to the invention is characterized in that the resilient means are provided with a resilient body having a first and second end between which, when they are moved further away from each other, a spring force increases, a first end being connected to the first body at a position which, in use, lies at an upper side of the forearm and the second end being connected to the second body at a position which, in use, is situated at an upper side of the hand. The resilient body applies a moment of force between the first and the second body, allowing the second body to hinge relative to the first body about the hinge situated between the two latter bodies. A particularly advantageous embodiment according to the invention is characterized in that the first body is provided with a first and second side wall situated opposite each other, the second body is provided with a first and second side wall situated apposite each other and the at least one hinge comprises a first and second hinge, the first hinge hinging the first side walls together around a rotation axis and the second hinging the second side walls together around the rotation axis. In a particular embodiment, the aid is further characterized in that the first and second hinge are each provided with the resilient means which press the first and second body relative to each other about the rotation axis to a predetermined position in which the first and second body include a predetermined angle, which angle is in a plane directed perpendicularly to the rotation axis.

The invention also provides a method for relaxing the extensor musculature through the principle of the flexor-extensor antagonism, wherein, by the exertion of forces on at least three pressure points on a forearm, the wrist of the forearm and the palm of the hand of the forearm, respectively, a moment of force is applied to the palm of the hand, such that the flexor musculature in the forearm must be flexed, as a result of which, due to the antagonism between the flexor musculature and the extensor musculature in the forearm, the extensor musculature is relaxed.

BRIEF DESCRIPTION OF THE DRAWINGS

The invention will presently be further elucidated with reference to the drawing. In the drawing:

FIG. 3b shows a perspective representation of the aid according to FIG. 3a;

DETAILED DESCRIPTION OF PREFERRED EMBODIMENTS

Figure 1:
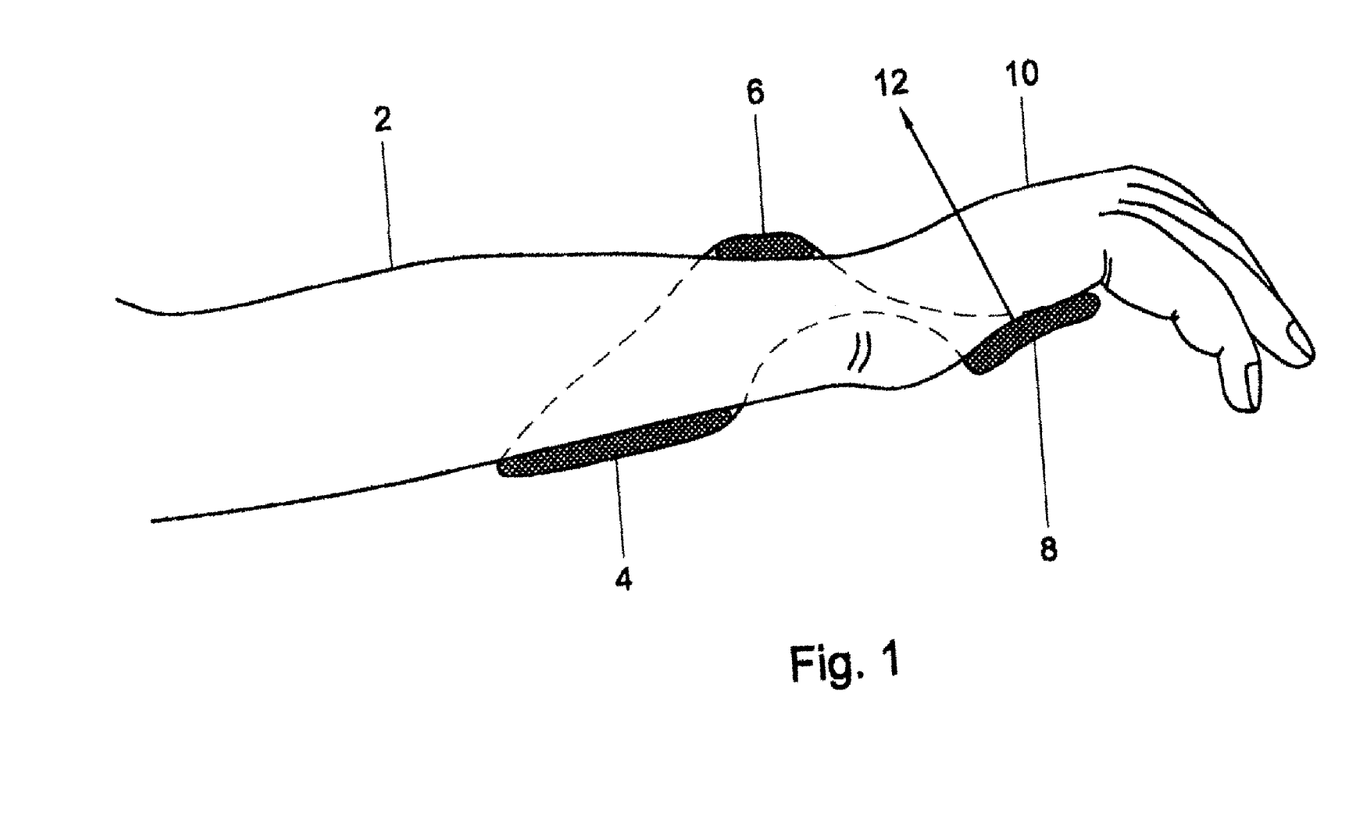
FIG. 1 schematically shows the principle of the invention for relaxing the extensor musculature by using at least three pressure points.
Figure 3A:
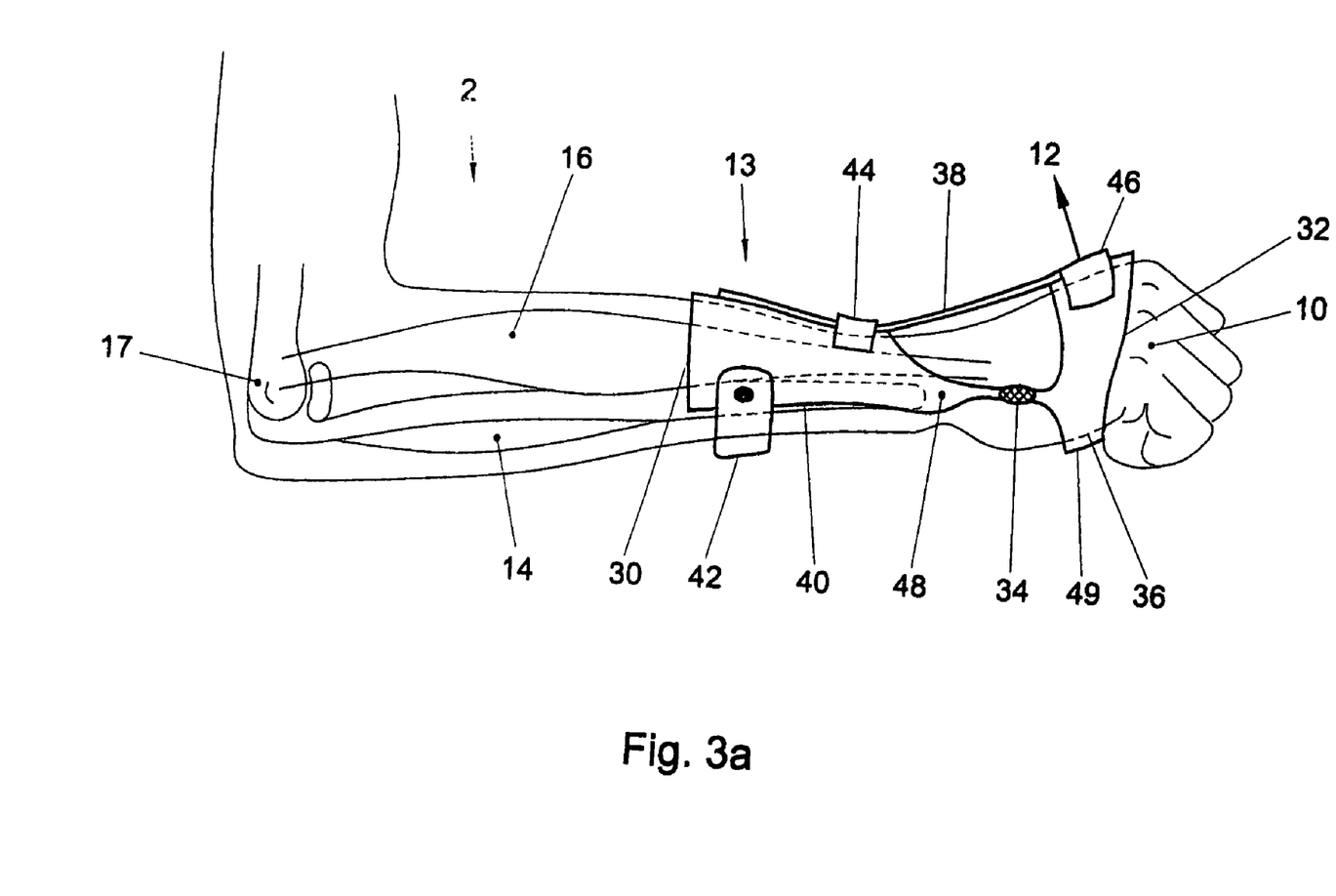
FIG. 3a schematically shows a side view of a first possible practical embodiment of an aid according to the invention.

FIG. 1 shows a forearm 2 on which three pressure points 4, 6 and 8 are indicated. The first pressure point 4 is located on the underside of the forearm, the second pressure point 6 is located on the wrist of the forearm and the third pressure point 8 lies against the palm of the hand of the hand 10. By applying forces to these at least three pressure points, a force component Faid 12 is applied to the palm of the hand, such that the hand 10 is pressed in a direction towards the upper side of the hand belonging to the palm of the hand. This is further elucidated in FIG. 3a. In FIG. 3a, an aid 13 is shown which is secured to a forearm 2. The flexor musculature 14 (flexor muscle) is a flexor which is in antagonistic action with the extensor musculature 16. The extensor musculature 16 (extensor muscle) is an extensor which is connected to the lateral epicondyle 17 in the elbow. The force component Faid 12 has as a result that flexor musculature 14 in the forearm 2 has to be flexed. As a result of the antagonistic action, which will be further elucidated below, the extensor musculature 16 will be physiologically relaxed. This relaxation is particularly important in case the extensor musculature is injured. A common injury of the extensor musculature is the so-called "tennis elbow". This injury results in pain stimuli which come from the origin of the extensor musculature according to the invention promotes recovery.

Figure 2A:
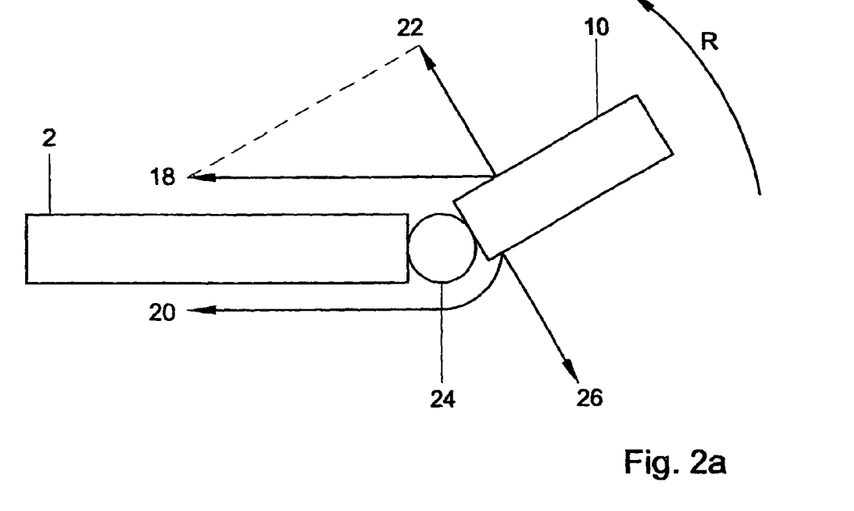
FIG. 2a shows a schematic overview of relevant forces and moments of force in the forearm without external force.
Figure 2B:
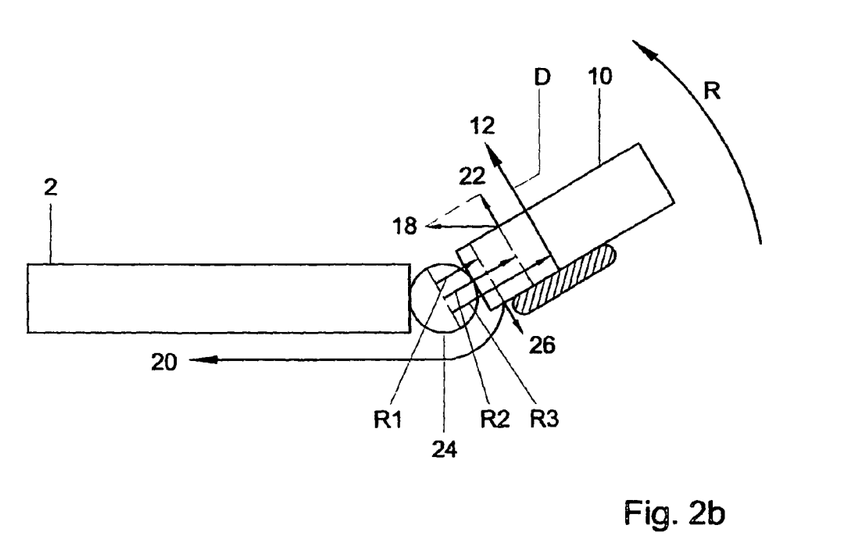
FIG. 2b shows a schematic overview of relevant forces and moments of force in the forearm with an external force of an aid according to the invention.

FIGS. 2a and 2b give a schematic overview of relevant forces and moments of force in the forearm 2. In FIG. 2a, no external force is incorporated. FIG. 2b does involve an external force, which is exerted, for instance, by an aid according to the invention.

FIG. 2a is a schematic overview of a forearm 2 with an associated hand 10. It is schematically indicated how a force Fext 18 is exerted by the extensor musculature, and a force Fflex 20 is exerted by the flexor musculature on the hand 10. There are no external forces working on the forearm. The force Fext 18 yields a force component, Fext, $\perp$ 22 perpendicular to the hand 10 relative to the wrist joint 24, which makes the hand 10 hinge in the direction of rotation R. The force Fflex 20 yields a force component Fext, $\perp$ 26 perpendicular to the hand 10, relative to the wrist joint 24, which makes the hand 10 hinge in a direction opposite to the direction of rotation R. FIG. 2b shows the result of the application of an external force component Faid 12 to the hand 10 (this force component is, for instance, generated by an aid according to the invention). To control the hand 10, there must almost be a near balance of moments of force relative to the joint 24. What applies here is that the flexor musculature should apply a moment of force (Fflex, $\perp$*R1) 26 which is almost equal to but opposite to the sum of the moments of force (Fext, $\perp$*R2) 22 and (Faid*R3) 12. (Wherein R1, R2 and R3 are the respective arms of the force components Fflex, $\perp$, Fext, $\perp$ and Faid, relative to the wrist joint 24). From the foregoing, it follows that the force component Fext, $\perp$ 22 generated by the extensor musculature will be smaller than in the case where the force component Faid 12 is not presented. The force Fext 18 which is exerted by the extensor musculature will also be smaller. In this way, the extensor musculature is physiologically relaxed through the flexor-extensor antagonism.

FIG. 3a shows the forearm 2 to which a possible practical embodiment of an aid 13 according to the invention is secured. The aid 13 for relaxing the extensor musculature 16 in the forearm is provided with a first body 30 and a second body 32. The aid further comprises at least one hinge joint 34 which hingedly connects the first aid second body. In this example, two hinges are involved. The first body 30 is arranged to be secured to a forearm 2 while the second body 32 extends from the hinge 34 to a palm of the hand 36 belonging to the forearm 2. Additionally, the aid is provided with resilient means 38 which, in use, generate a moment of force between the first and second body relative to the hinge (and hence relative to the rotation axis of the two bodies), such that the second body 32, hinging relative to the first body 30, presses against the palm of the hand 36 in a direction directed towards the upper side of the hand belonging to the palm (this direction is indicated in FIG. 2*b* with the vector D12). The aid 13 in FIG. 3*a* comprises a first body 30 which is of substantially tubular design and is provided with a channel-shaped member 40 of a rigid material and a first elastically adjustable strap 42 which is connected to the channel-shaped member 40. The channel-shaped member 40 is arranged to embrace, in use, at least a part of an upper side of the forearm 2, while the first strap 42 bridges an open longitudinal side of the channel-shaped member, thereby passing over at least a part of an underside of the forearm. The first strap 42 can be provided with a fastening mechanism comprising, for instance, a hook a loop type tape or clasps, such as VELCRO®.

Figure 3B:
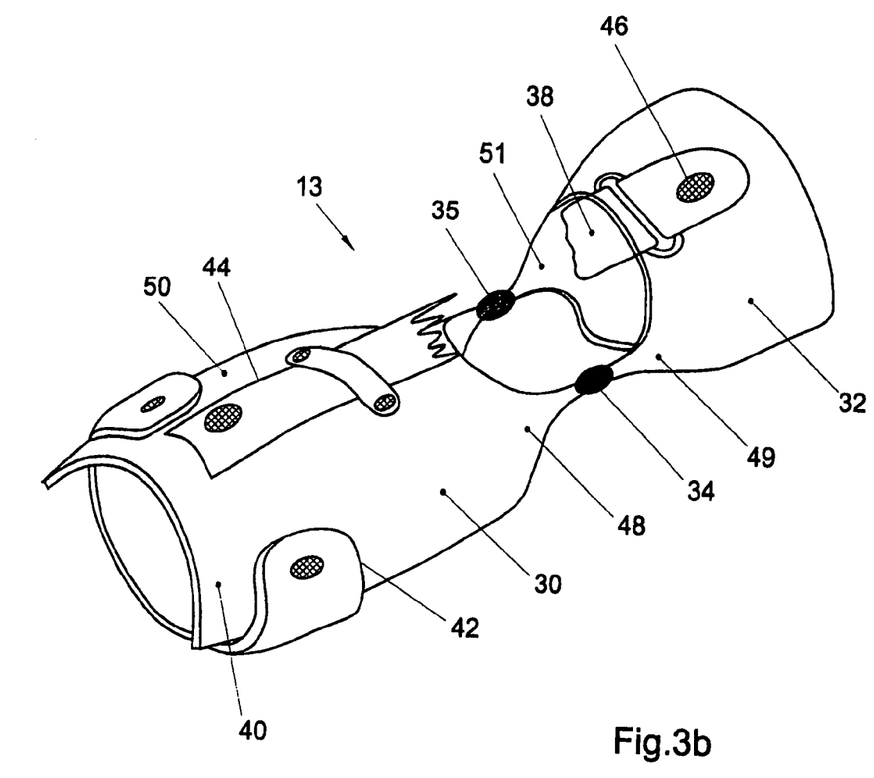
Figure 4:
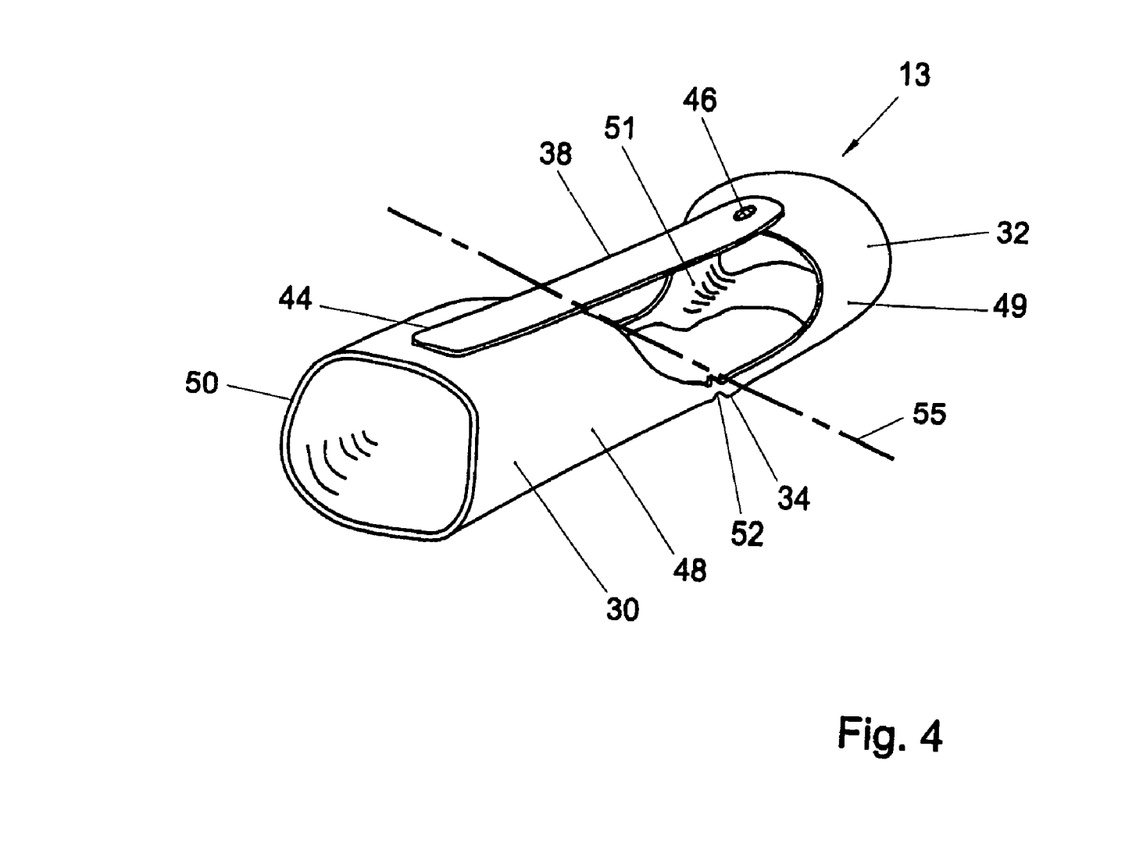
FIG. 4 shows a first alternative embodiment of the aid according to the invention.

The second body 32 of the aid 13 is arranged to embrace the part of the hand 10 situated between the index finger and the little finger. According to the embodiment of FIG. 3*a*, the second body 32 is substantially tubular and made of a rigid material. The hand 10 is preferably not completely covered, so that the hand is restricted as little as possible in its gripping function by the aid 13 secured to the forearm 2. Further, the resilient means are designed as a resilient body 38. This resilient body 38 comprises a first and a second end between which a spring force increases when they are moved further away from each other. The resilient body 38 can be an elongate elastic material (such as an elastic). The first end of the resilient body 38 is attached to the first body 30, at a position 44, which, in use, lies at an upper side of the forearm. The second end is connected with the second body 32 at a position 46, which, in use, lies at an upper side of the hand. In a further elaborated embodiment according to FIG. 3*a*, the first body 30 is provided with a first side wall 48 and a second side wall 50 which are situated opposite each other (see FIG. 3*b*). The second body 32 is provided with a first side wall 49 and an opposite second side wall 51. The aid 13 here comprises a first hinge 34 and a second hinge 35 which are situated opposite each other on either side of the wrist. The first hinge 34 hingedly connects the first side wall 48 of the first body 30 with the first side wall 49 of the second body 32 about a rotation axis (this rotation axis is substantially perpendicular to the plane of the drawing of FIG. 3*a*). The second hinge 35 hingedly connects the second side wall 50 of the first body 30 to the second side wall 51 of the second body about the rotation axis mentioned. In FIG. 4, a first alternative embodiment of an aid according to the invention is shown. In this embodiment of the aid 13, the first body 30 is of a substantially tubular design and manufactured from a rigid material. The tubular first body 30 is arranged to embrace a forearm. The second body 32 is arranged to embrace the part of the hand of the forearm situated between the index finger and the little finger, this second body 32 being of substantially tubular design and manufactured from a rigid material. In a further elaborated embodiment accosting to FIG. 4, the first body 30 is provided with a first side wall 48 and a second side wall 50, situated opposite each other. The second body 32 is provided with a first side wall 49 and an opposite second side wall 51. The aid 13 here comprises a first hinge 52 and a second hinge which are situated opposite each other on either side of the arm. The first hinge 52 hingedly connects the first side wall 48 of the first body 30 to the first side wall 49 of the second body 32 about a rotation axis. The rotation axis is indicated in FIG. 4 with reference numeral 55. The second hinge hingedly connects the second side wall 50 of the first body 30 to the second side wall 51 of the second body 32 about the rotation axis mentioned. The aid 13 further comprises resilient means which are provided with a resilient body 38 having a first and second end between which a spring force increases when they are moved-further away from each other. The first end of the resilient body 38 is attached to the first body at a position 44 which, in us, lies at an upper side of the forearm, and the second end is connected to the second body at a position 46 which, in use, lies at an upper side of the hand.

Figure 5:
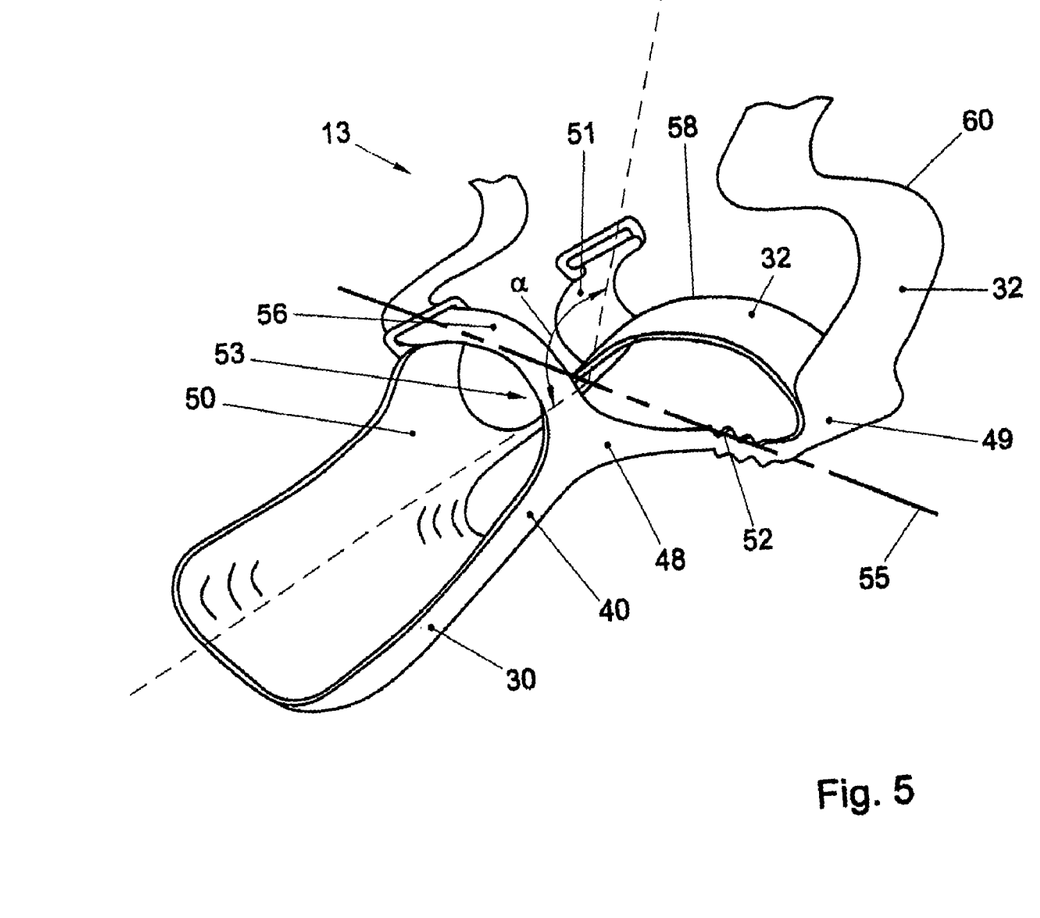
FIG. 5 shows a second alternative embodiment of the aid according to the invention.

The resilient body 38 can also include a memory metal. In this example, the memory metal comprises a memory alloy in austenitic condition. In use, when the hand is extended around the wrist joint in line with the forearm, the resilient body 38 exerts a moment of force on the hand. The memory metal has as a property that when, for instance, taking as a starting the resilient body 38 is extended in the direction of rotation R as shown in FIG. 3*a*, or, conversely, are bent in a direction of rotation opposite to the direction R as shown in FIG. 3*a*, the moment of force exerted on the palm of the hand will change little. The material chosen has the properties specific for memory metal in austenitic form, i.e. large elastic deformation is possible (8% or more, so-called superelasticity). Further, a very low modulus of stiffness is involved when the material stress reaches the so-called plateau stress. In FIG. 5, a second alternative embodiment of the aid 13 according to the invention is given. Here, the first body 30 of the aid 13 is of a substantially tubular design and is provided with a channel-shaped member 40 of a rigid material and a flexible strap 56. The channel-shaped member 40 is connected to the first flexible strap 56 and is arranged to embrace, in use, at least a, part of an underside of a forearm. The first strap 56 bridges an open, longitudinal side of the channel-shaped member 40 and passes over at least a part of an upper side of the forearm. The second body is arranged to embrace the part of the hand situated between the index finger and the little finger, to which end the second body is of a substantially tubular design. Further, the second body is provided with a pressure member 58 of a rigid material and a flexible second strap 60 which is connected to the pressure member 58. The pressure member 58 is arranged to abut, in use, at least partly, against the palm of the hand, while the second strap 60 passes over the back of the hand. Preferably, the first and second strap are provided with a fastening mechanism comprising, for instance, a hook an loop type tape or clasps, such as VELCRO®. In a further elaborated embodiment according to FIG. 5, the first body 30 is provided with a first side wall 48 and a second side wall 50, situated opposite each other. The second body 32 is provided, with a first side wall 49 and an opposite, second side wall 51. The aid here comprises a first hinge 52 and a second hinge 53, situated opposite each other. The first hinge 52 hingedly connects the first side wall 48 of the first body 30 to the first side wall 49 of the second body around a rotation axis. The second hinge 53 hingedly connects the second side wall 50 of the first body 30 to the second side wall 51 of the second body 32 around the rotation axis 55. In this embodiment, the first hinge 52 and the second hinge we each provided with resilient means which press the first body 30 and the second body 32 relative to each other about the rotation axis 55 to a predetermined position in which the first and second body include a predetermined angle α. This angle α is in a plane perpendicular to the rotation axis 55. In FIG. 5, this angle α is schematically indicated by means of two dotted lines. These dotted lines indicate the positions of the first body 30 and the second body 32 of the aid 13 relative to each other when the aid 13 is in the initial or rest position. (In FIG. 5, the aid 13 is not represented in the position of rest. The position represented in FIG. 5 can be achieved from the position of rest by applying an external moment of force between the first body and the second body).

Figure 6A:
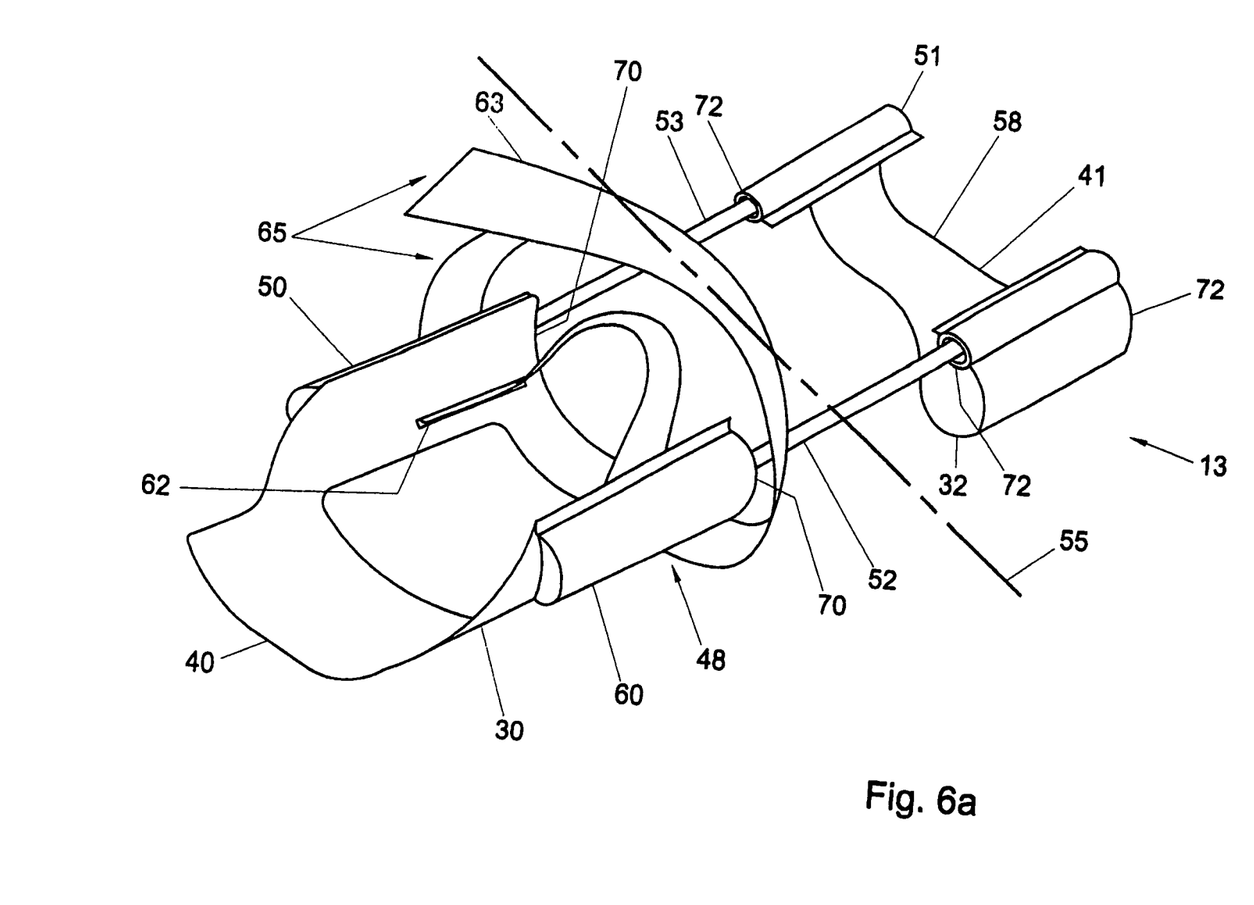
FIG. 6a shows a third alternative embodiment of the aid according to the invention in a condition in which it is worn.
Figure 6B:
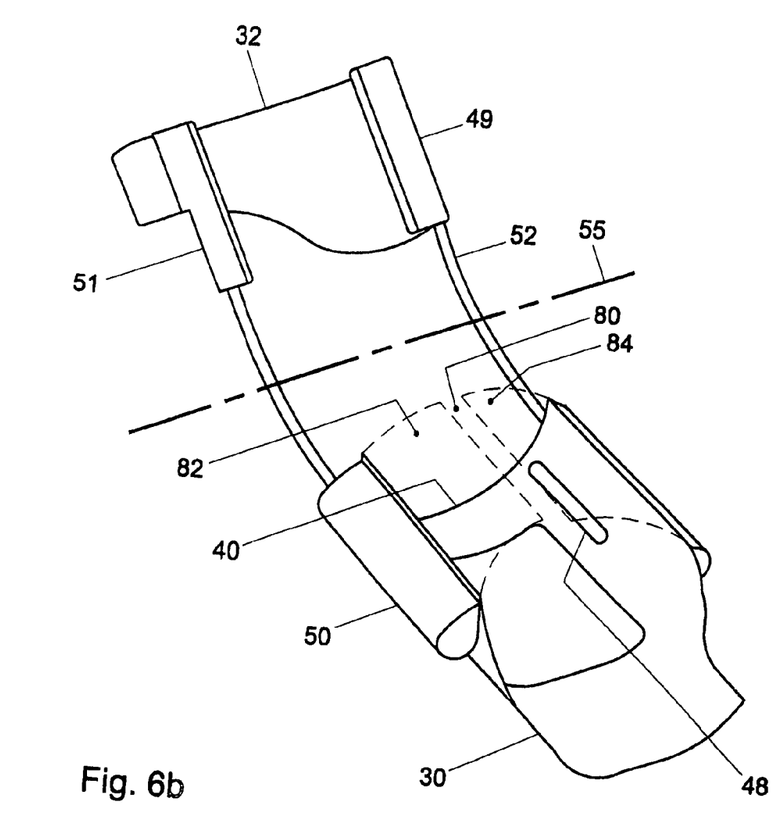
FIG. 6b shows the aid of FIG. 6a in a relaxed condition when, it is not worn.

In FIGS. 6a and 6b, a third alternative embodiment of an aid according to the invention is shown, in which parts corresponding to the preceding figures are provided with the same reference numerals. In the device according to FIGS. 6a and 6b, the first body 30 is provided with a first channel-shaped member 40. The channel-shaped member is further provided with a first side wall 48 and a second side wall 50. In the first and second side wall 48, 50, slotted openings 60, 62 are provided. Through these openings, a strap 63 can be laced, such that it extends over an upper side of a forearm of a user for securing the first body 30 to the forearm. For closing the strap in a loop-shape, the ends of the strap can, for instance, be provided with a hook and loop type tape, such as VELCRO®.

In this example, the second body 32 is likewise provided with a second channel-shaped member 41. The second channel-shaped member 41 is provided with two side walls 49, 51, situated opposite each other. The second body also comprises a pressure member 58 arranged to lie, in use, at least partly against the palm of the hand. In particular, this part of the second channel-shaped member extends, in use, between a part of the inside of the hand situated between the index finger and the little finger. This part of the channel-shaped member lies against this part of the hand and presses against it. The aid further comprises a first and second hinge 52, 53, the first hinge 52 hingedly connecting the first side walls 48, 49 to each other and the second hinge 63 hingedly connecting the two side walls 50, 51 to each other. In this example, the first side walls 48, 49 and the second side walls 50, 51 are pivotally connected to each other around an imaginary rotation axis 55.

The first hinge 52 is provided with a first metal resilient bar-shaped member 52 having a first and second end 70, 72 which are connected to the first side wall 48 and the second side wall 49, respectively. The second hinge is likewise provided with a, in this case second, metal resilient liar-shaped member 53 having a first and second end 70, 72, which are connected to the second side walls 50, 51, respectively. The first and second metal bar-shaped members 52, 53 also form the earlier-mentioned resilient means.

In the example, the first and second bar-shaped member 52, 53 are manufactured from memory metal. In this example, the memory metal comprises a memory alloy in austenitic condition.

When the aid is not in use and the resilient means 52, 53 are relaxed, the aid is in a condition as shown its FIG. 6b. In use, the aid is in a condition according to FIG. 6a when the hand is extended around the wrist joint in line with the forearm. The moment of force referred to is then exerted on the hand.

The memory metal has as a property that when, for instance, taking as a starting point the condition in FIG. 6a, the resilient means 52, 53 are bent in the direction of rotation R as shown in FIG. 3a, or, conversely, are bent in a direction of rotation opposite to the direction R as shown in FIG. 3a, the moment of force exerted on the palm of the hand will change little. The material chosen has the properties specific for memory metal in austenitic form, i.e. large elastic deformation is possible (8% or more, so-called superelasticity). Further, a very low modulus of stiffness is involved when the material stress reaches the so-called plateau stress.

Starting from the condition in FIG. 6a, when the aid is worn by a user, the moment of force will only decrease slowly, that is, little, when the second body is moved in the direction R, as shown in FIG. 3a relative to the first body, or when the second body is moved relative to the first body in a direction opposite to the direction R of FIG. 3a. It follows that a fairly constant flexiforce (moment of force) is exerted on the hand which is reasonably independent of the position, i.e. the position the hand takes relative to the forearm.

Furthermore, lax particular with the above-mentioned choice of material, the first and second bar-shaped member can have a length of 40 mm to 120 mm. Further, the first and the second bar-shaped member can have a diameter of 0.5 to 2 mm.

The first body 30 can be manufactured from, for instance, a semi-rigid plastic material which has been conformed to the forearm of the patient by heating. The second body can also be manufactured from a semi-rigid plastic which has been conformed to the hand of the patient by heating.

In the example of FIG. 6a, mention is made, of a first channel-shaped member 44 provided with the flexible strap 63. The flexible strap 63 and the channel-shaped member 40 together form a tubular member which can embrace the forearm completely. In the present patent application, the term channel-shaped member therefore encompasses a first body of a tubular design. In particular, also the strap 63 can be replaced with the same material as that from which the channel-shaped member 40 is manufactured. In that case, a tube made in one piece from plastic as shown in FIG. 4 is obtained. What holds true for the first body 30, also holds true, by analogy, for the second body 32, which, accordingly, can also be of tubular design and the term channel-shaped, in this context, encompasses a tubular shape.

It is also conceivable that the first body 30 has a tubular design, wherein, in the first body at its upper side, i.e. the side which, in use, is on top of the forearm, a cut 80 is provided. This arrangement is schematically shown in FIG. 6b. Parts 82, 84 can then be bent away from each other to enlarge the cut 80 to position the first body 30 around the arm. The pressure point 6 shown in FIG. 1 is an imaginary pressure point in this example, which is formed in combination by symmetrical forces between the first body and the forearm. Such variants are all understood to fall within the scope of the invention.

The invention has been described on the basis of a few preferred embodiments, but, as will be evident to the skilled person, many embodiments are possible which also fall within the scope of the invention. It is possible, for instance, to design the aid in all possible combinations of the above described embodiments of the first and the second body of the aid. These embodiments can be realized in different sizes in a version for the left as well as for the right arm. Further, there are various alternatives with which the resilient means can be provided, it being possible, for instance, that the resilient means comprise a leaf spring (resilient means also encompass resilient means causing a rotation to extension, both through pull forces and pressure forces). The resilient means can be incorporated in the hinge.

The invention claimed is:
1. An aid for relaxing the extensor musculature in the forearm comprising, a first body, a second body and at least one hinge joint hinging the first and second body together, wherein the first body has structure arranged to be secured to a forearm with the second body extending from the hinge to a palm of the hand belonging to the forearm, the aid further comprising a resilient member, which in use, generates a moment of force between the first and second body, such that the second body via the hinge presses against the palm of the hand in a direction directed towards the upper side of the hand belonging to the palm, and wherein the resilient member contains a memory metal, such that the moment of force exerted on the palm of the hand is a substantially constant flexiforce, independent of the position the hand takes around the wrist joint relative to the forearm.

2. An aid according to claim 1, wherein the first body is provided with a first channel-shaped member of a rigid material.

3. An aid according to claim 2, wherein the first channel-shaped member is arranged to embrace, in use, at least a part of an underside of the forearm.

4. An aid according to claim 2, wherein the first channel-shaped member is provided with a first and second side wall situated opposite each other, the second body is provided with a second channel-shaped member having a first and second side wall situated opposite each other, and the at least one hinge comprises a first and second hinge, the first hinge hinging the first side walls together about a rotation axis and the second hinge hinging the second side walls together about the rotation axis.

5. An aid according to claim 4, wherein the first hinge is provided with a first metal resilient bar-shaped member having a first and second end which are connected to the first side walls of the first and second channel-shaped members, respectively, and the second hinge is provided with a second metal resilient bar-shaped member having a first and second end connected with the second side walls of the first and second channel-shaped members, respectively, wherein the first and second bar-shaped members form the resilient member.

6. An aid according to claim 5, wherein the first and second bar-shaped members are made of a memory metal.

7. An aid according to claim 5, wherein the first and second bar-shaped member has a length of from 40 mm to 120 mm.

8. An aid according to claim 5, wherein the first and second bar-shaped member has a diameter of form, 0.5 mm to 2 mm.

9. An aid according to claim 1, wherein the second body is provided with a second channel-shaped member of a rigid material.

10. An aid according to claim 9, wherein the second channel-shaped member is arranged to abut, in use, against at least a part of an inside of the hand situated between the index finger and the little finger.

11. An aid according to claim 1, wherein the memory metal comprises a memory alloy in austenitic condition.

12. An aid according to claim 1, wherein the first body is of substantially tubular design and includes a channel-shaped member of a rigid material and a first elastically adjustable strap which, is connected to the channel-shaped member, wherein the channel-shaped member is arranged to embrace, in use, at least a part of an upper side of the forearm while the first strap bridges an open longitudinal side of the channel-shaped member, thereby passing over at least a part of an underside of the forearm.

13. An aid according to claim 12, wherein the first strap is provided with a fastening mechanism.

14. An aid according to claim 12, wherein the second body is arranged to embrace the part of the hand situated between the index finger and the little finger.

15. An aid according to claim 14, wherein the second body has a substantially tubular design and is provided with a pressure element of a rigid material and a second elastically adjustable strap which is connected to the pressure element, the pressure element being arranged to abut, in use, at least partly against the palm of the hand while the second strap passes over the back of the hand.

16. An aid according to claim 15, wherein the second strap is provided with a fastening mechanism.

17. An aid according to claim 16, wherein the second body has a substantially tubular design and is manufactured from a rigid material.

18. An aid according to claim 12, wherein the resilient member is provided with a resilient body having a first and a second end between which a spring force increases when the ends are moved further away from each other, wherein a first end is connected to the first body at a position which, in use, lies at an upper side of the forearm and wherein the second end is connected to the second body at a position which, in use, lies at an upper side of the hand.

19. An aid according to claim 12, wherein the first body is provided with a first and second side wall situated opposite each other, the second body is provided with a first and second side wall situated opposite each other and the at least one hinge comprises a first and second binge, the first hinge hinging the first side walls together about a rotation axis and the second binge hinging the second side walls together about the rotation axis.

20. An aid according to claim 19, wherein the first and second hinge each are provided with the resilient member which presses the first and second body relative to each other about the rotation axis to a predetermined position in which the first and second body are disposed at a predetermined angle lying in a plane perpendicular to the rotation axis.

21. An aid according to claim 12, wherein the resilient member is composed of a spring having a first and a second end and, wherein a first end is connected to the first body at a position which, in use, lies at an upper side of the forearm and wherein the second end is connected to the second body at a position which, in use, lies at an upper side of the hand.

22. An aid according to claim 1, wherein the first body is of substantially tubular design and is provided with a channel-shaped member of a rigid material and a first elastically adjustable strap which, is connected to the channel-shaped member, wherein the channel-shaped member is arranged, to embrace, in use, at least a part of an underside of the forearm while the first strap bridges an open longitudinal side of the channel-shaped, member, thereby passing over at least a part of an upper side of the forearm.

23. An aid according to claim 1, wherein the first body has a substantially tubular design and is made of a rigid material, the tubular first body being arranged to embrace the forearm.

24. A method for relaxing the extensor musculature through the principle of the flexor-extensor antagonism, wherein, through the application of forces to at least three pressure points on a forearm, the wrist of the forearm and the palm of the hand of the forearm, respectively, a moment of force is applied to the palm of the hand, such that the flexor musculature (flexors) in the forearm must be flexed, so that, as a result of the antagonism between the flexor musculature and the extensor musculature in the forearm, the extensor musculature is relaxed, wherein the moment of force exerted on the palm of the hand is a substantially constant flexiforce, independent of the position the hand takes around the wrist joint relative to the forearm, and wherein a memory alloy exerts the moment of force on the palm of the hand.

* * * * *